(12) United States Patent
Vick et al.

(10) Patent No.: US 8,759,615 B2
(45) Date of Patent: Jun. 24, 2014

(54) TRANSFORMATION OF ALGAL CELLS

(75) Inventors: Bertrand Vick, Emeryville, CA (US); Oliver Kilian, Alameda, CA (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 13/372,467

(22) Filed: Feb. 13, 2012

(65) Prior Publication Data

US 2012/0208279 A1     Aug. 16, 2012

Related U.S. Application Data

(63) Continuation of application No. 12/480,611, filed on Jun. 8, 2009, now Pat. No. 8,119,859.

(60) Provisional application No. 61/059,672, filed on Jun. 6, 2008.

(51) Int. Cl.
| | |
|---|---|
| C12N 15/87 | (2006.01) |
| C12P 7/64 | (2006.01) |
| C12N 15/82 | (2006.01) |
| C12N 1/12 | (2006.01) |
| C12N 1/13 | (2006.01) |

(52) U.S. Cl.
CPC ........ C12N 15/8206 (2013.01); C12N 15/8247 (2013.01)
USPC ..... 800/292; 800/281; 435/257.2; 435/257.3; 435/470

(58) Field of Classification Search
None
See application file for complete search history.

(56) References Cited

U.S. PATENT DOCUMENTS

| | | | |
|---|---|---|---|
| 1,926,780 | A | 9/1933 | Lippincott |
| 3,468,057 | A | 9/1969 | Buisson |
| 3,962,466 | A | 6/1976 | Nakabayashi |
| 4,003,337 | A | 1/1977 | Moore |
| 4,267,038 | A | 5/1981 | Thompson |
| 4,365,938 | A | 12/1982 | Warinner |
| 4,535,060 | A | 8/1985 | Comai |
| 4,658,757 | A | 4/1987 | Cook |
| 5,105,085 | A | 4/1992 | McGuire et al. |
| 5,478,208 | A | 12/1995 | Kasai et al. |
| 5,527,456 | A | 6/1996 | Jensen |
| 5,661,017 | A | 8/1997 | Dunahay et al. |
| 5,668,298 | A | 9/1997 | Waldron |
| 5,723,595 | A | 3/1998 | Thompson et al. |
| 5,823,781 | A | 10/1998 | Hitchcock et al. |
| 6,027,900 | A | 2/2000 | Allnutt et al. |
| 6,117,313 | A | 9/2000 | Goldman |
| 6,143,562 | A | 11/2000 | Trulson et al. |
| 6,166,231 | A | 12/2000 | Hoeksema |
| 6,297,054 | B1 | 10/2001 | Maliga et al. |
| 6,372,460 | B1 | 4/2002 | Gladue et al. |
| 6,448,055 | B1 | 9/2002 | Shimizu et al. |
| 6,736,572 | B2 | 5/2004 | Geraghty |
| 6,750,048 | B2 | 6/2004 | Ruecker et al. |
| 6,831,040 | B1 | 12/2004 | Unkefer et al. |
| 6,871,195 | B2 | 3/2005 | Ryan et al. |
| 7,244,609 | B2 | 7/2007 | Drocourt et al. |
| 7,381,326 | B2 | 6/2008 | Haddas |
| 7,410,637 | B2 | 8/2008 | Sayre et al. |
| 7,449,568 | B2 | 11/2008 | Fukuda et al. |
| 7,547,551 | B2 | 6/2009 | Schuler et al. |
| 8,039,230 | B2 | 10/2011 | Otte et al. |
| 8,119,859 | B2 | 2/2012 | Vick et al. |
| 8,314,228 | B2 | 11/2012 | Kilian et al. |
| 8,318,482 | B2 | 11/2012 | Vick et al. |
| 2003/0049720 | A1 | 3/2003 | Hoshino et al. |
| 2003/0140021 | A1 | 7/2003 | Ryan et al. |
| 2003/0143743 | A1 | 7/2003 | Schuler et al. |
| 2003/0199490 | A1 | 10/2003 | Antoni-Zimmermann et al. |
| 2003/0211089 | A1 | 11/2003 | Sayre et al. |
| 2004/0161364 | A1 | 8/2004 | Carlson |
| 2004/0262219 | A1 | 12/2004 | Jensen |
| 2005/0064577 | A1 | 3/2005 | Berzin |
| 2005/0095569 | A1 | 5/2005 | Franklin |
| 2005/0124010 | A1 | 6/2005 | Short et al. |
| 2005/0170479 | A1 | 8/2005 | Weaver et al. |
| 2005/0181345 | A1 | 8/2005 | Bradbury et al. |
| 2005/0260553 | A1 | 11/2005 | Berzin |
| 2006/0031087 | A1 | 2/2006 | Fox |

(Continued)

FOREIGN PATENT DOCUMENTS

| | | |
|---|---|---|
| CN | 1627764 | 6/2005 |
| CN | 1867140 | 11/2006 |

(Continued)

OTHER PUBLICATIONS

Geng et al. Acta Botanica Sinica 46(3): 342-346 (2004).*
Chen et al. Current Genetics 39(5-6): 365-370 (Jul. 2001).*
Suga et al. Journal of Electrostatics 64(12): 796-801 (Nov. 2006).*
Chen et al. Journal of Phycology 44: 768-776 (2008).*
Santin-Montanya, I. "Optimal Growth of *Dunaliella Primolecta* in Axenic Conditions to Assay Herbicides," Chemosphere, 66, Elsevier 2006, p. 1315-1322.
Felix, R. "Use of the cell wall-less alga *Dunaliella bioculata* in herbicide screening tests," Annals of Applied Biology, 113, 1988, pp. 55-60.
Janssen, M. "Phytosynthetic efficiency of *Dunaliella tertiolecta* under short light/dark cycles," Enzyme and Microbial Technology, 29, 2001, p. 298-305.

(Continued)

*Primary Examiner* — David T Fox
(74) *Attorney, Agent, or Firm* — Carr & Ferrell LLP (57) ABSTRACT

Exemplary methods include a method for transforming an algal cell by preparing a transformation construct, preparing a particle for bombarding the algal cell, adhering the transformation construct to the particle, bombarding the algal cell with the particle, and growing the algal cell into a colony. The transformation construct is replicated within a nuclear genome of the algal cell and the growing of the algal cell is in a nutrient medium. Another exemplary method may include a method for genetically modifying an algal cell, by adding nucleic acid to the algal cell while the algal cell is suspended in a solution of low conductivity, introducing the nucleic acid into the algal cell by application of an electrical pulse resulting in a transformed algal cell, and selecting a colony that includes the transformed algal cell.

5 Claims, 7 Drawing Sheets

(56) References Cited

U.S. PATENT DOCUMENTS

| | | |
|---|---|---|
| 2006/0044259 A1 | 3/2006 | Hotelling et al. |
| 2006/0045750 A1 | 3/2006 | Stiles |
| 2006/0101535 A1 | 5/2006 | Forster et al. |
| 2006/0122410 A1 | 6/2006 | Fichtali |
| 2006/0155558 A1 | 7/2006 | Corpening |
| 2006/0166243 A1 | 7/2006 | Su et al. |
| 2006/0166343 A1 | 7/2006 | Hankamer et al. |
| 2006/0192690 A1 | 8/2006 | Philipp |
| 2007/0178451 A1 | 8/2007 | Deng et al. |
| 2008/0118964 A1 | 5/2008 | Huntley et al. |
| 2008/0120749 A1 | 5/2008 | Melis et al. |
| 2008/0160488 A1 | 7/2008 | Younkes et al. |
| 2008/0160591 A1 | 7/2008 | Willson et al. |
| 2008/0194029 A1 | 8/2008 | Hegemann et al. |
| 2008/0268539 A1 | 10/2008 | Singh et al. |
| 2008/0293132 A1 | 11/2008 | Goldman et al. |
| 2009/0029445 A1 | 1/2009 | Eckelberry et al. |
| 2009/0061493 A1* | 3/2009 | Trimbur et al. ............... 435/157 |
| 2009/0061928 A1 | 3/2009 | Lee et al. |
| 2009/0148931 A1 | 6/2009 | Wilkerson et al. |
| 2009/0234146 A1 | 9/2009 | Cooney et al. |
| 2009/0317857 A1 | 12/2009 | Vick et al. |
| 2009/0317878 A1 | 12/2009 | Champagne et al. |
| 2009/0317904 A1 | 12/2009 | Vick et al. |
| 2009/0319338 A1 | 12/2009 | Parks et al. |
| 2009/0325270 A1 | 12/2009 | Vick et al. |
| 2010/0068772 A1 | 3/2010 | Downey |
| 2010/0100520 A1 | 4/2010 | Dargue et al. |
| 2010/0198659 A1 | 8/2010 | Meltzer et al. |
| 2010/0210003 A1 | 8/2010 | King |
| 2010/0210832 A1 | 8/2010 | Kilian et al. |
| 2010/0314324 A1 | 12/2010 | Rice et al. |
| 2010/0323387 A1 | 12/2010 | Bailey et al. |
| 2010/0330643 A1 | 12/2010 | Kilian et al. |
| 2011/0015415 A1 | 1/2011 | Singh et al. |
| 2011/0059495 A1 | 3/2011 | Bailey et al. |
| 2011/0091977 A1 | 4/2011 | Kilian et al. |
| 2012/0190115 A1 | 7/2012 | Kilian et al. |
| 2013/0102040 A1 | 4/2013 | Radakovits et al. |
| 2013/0131330 A1 | 5/2013 | Kilian et al. |

FOREIGN PATENT DOCUMENTS

| | | |
|---|---|---|
| CN | 1956335 | 5/2007 |
| CN | 101289659 | 10/2008 |
| WO | WO2004106238 A2 | 12/2004 |
| WO | WO2007084078 A1 | 7/2007 |
| WO | WO2008060571 A2 | 5/2008 |
| WO | WO2008106803 A1 | 9/2008 |
| WO | WO2008060571 A3 | 11/2008 |
| WO | WO2008060571 A8 | 2/2009 |
| WO | WO2009124070 A1 | 10/2009 |
| WO | WO2009149470 A1 | 12/2009 |
| WO | WO2010011335 A1 | 1/2010 |
| WO | WO2011011463 A2 | 1/2011 |
| WO | WO2011049995 A1 | 4/2011 |

OTHER PUBLICATIONS

Saenz, M.E., "Effects of Technical Grade and a Commercial Formulation of Glyphosate on Algal Population Growth," Bulletin of Environmental Contamination Toxicology, 1997, 59: pates 638-644.

Christy et al., "Effects of Glyphosate on Growth of *Chlorella*," Weed Science, vol. 29, Issue 1, Jan. 1981, pp. 5-7.

Roessler et al., "Genetic Engineering Approaches for Enhanced Production of Biodiesel Fuel from Microalgae," ACS Symposium Series; American Chemical Society, 1994, pp. 255-270.

Endo et al. "Inactivation of Blasticidin S by *Bacillus Cereus* II. Isolation and Characterization of a Plasmid, pBSR 8, from *Bacillus Cereus*," The Journal of Antibiotics 41 (2): 271-2589-2601.

Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).

Kindle et al. "Stable Nuclear Transformation of Chlamydomonas Using the Chlamydomonas Gene for Nitrate Reductase" The Journal of Cell Biology 109 (6, part 1): 2589-2601, (1989).

Prein et al. "A Novel Strategy for Constructing N-Terminal Chromosomal Fusions to Green Fluorescent Protein in the Yeast *Saccharomyces cerevisiae*" FEBS Letters 485 (2000) 29-34.

Schiedlmeier et al., "Nuclear Transformation of *Volvox Carteri*" Proceedings of the National Academy of Sciences USA 91(11): 5080-5084 (May 1994).

Wendland et al. "PCR-Based Methods Facilitate Targeted Gene Manipulations and Cloning Procedures" Curr.Gen. (2003) 44:115-123.

Molnar et al., "Highly Specific Gene Silencing by Artificial MicroRNAs in the Unicellular Agla *Chlamydomonas reinhardtii*," Plant Jour. ePub Jan. 17, 2009, vol. 58, No. 1, pp. 157-164 (Abstract Only).

Nelson et al., "Targeted Disruption of NIT8 Gene in *Chlamydomonas reinhardtii*." Mol. Cell. Bio. Oct. 1995, vol. 15, No. 10, pp. 5762-5769.

Kureshy et al., "Effect of Ozone Treatment on Cultures of *Nannochloropsis oculata*, *Isochrysis galbana*, and *Chaetoceros gracilis*," Journal of the World Aquaculture Society, 1999, 30(4), pp. 473-480.

Genbank Accession No. U71602 (*Nannochloropsis sp.* Violaxanthing/chlorophyll a binding protein precursor (NANVCP) mRNA, 1996.

Sukenik et al. "Characterization of a Gene Encoding the Light-Harvesting Violaxanthin-Chlorophyll Protein of *Nannochloropsis Sp.* (Eustigmatophyceae)," Journal of Phycology, Jun. 2000; 36(3), pp. 563-570.

Abe et al., AG610981, *Musmusculus molossinus* DNA, 2004.

Kopczynski et al., CO268749, *Drosophila melanogaster* cDNA clone EK092604, 2004.

Csogor et al., "Light Distribution in a Novel Photobioreactor—Modelling for Optimization," Journal of Applied Phycology, vol. 13, pp. 325-333 (2001).

Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.

Zittelli et al., "Mass Cultivation of *Nannochloropsis Sp.* In Annular Reactors," Journal of Applied Phycology, vol. 15, pp. 107-113, Mar. 2003.

Strzepek et al., "Photosynthetic Architecture Differs in Coastal and Oceanic Diatoms," Nature, vol. 431, pp. 689-692, Oct. 2004.

Shi et al., "Analysis of Expressed Sequence Tags from the Marine Microalga *Nannochloropsis Oculata* (eustigmatophyceae)," Journal of Phycol, vol. 44, pp. 99-102, 2008.

Thiel et al., "Transformation of a Filamentous Cyanobacterium by Electroporation," Journal of Bacteriology, Oct. 1989, vol. 171, No. 10, pp. 5743-5746.

Krienitz et al., "*Nannochloropsis limnetica* (Eustigmatophyceae), a new species of picoplankton from freshwater," Phycologia, 2000, vol. 39, No. 3, Abstract.

Lee et al., "Isolation and Characterization of a Xanthophyll Aberrant Mutant of the Green Alga *Nannochloropsis oculata*," Marine Biotechnology, 2006, vol. 8, pp. 238-245.

Sukenik et al., "Regulation of Fatty Acid Composition by Irradiance Level in the Eustigmatophyte *Nannochloropsis*," Journal of Phycol., 1989, vol. 25, pp. 686-692.

Rocha et al., "Growth Aspects of the Marine Microalga *Nannochlorpsis gaditana*," Biomolecular Engineering, 2003, vol. 20, pp. 237-242.

MacIntyre et al., "Primary Production by Suspended and Benthic Microalgae in a Turbid Estuary: Time-Scales of Variability in San Antonio Bay, Texas," Marine Ecology Progress Series, 1996, vol. 145, pp. 245-268.

Dunahay et al, "Manipulation of Microalgal Lipid Production Using Genetic Engineering," Applied Biochemistry and Biotechnology, 1996, vol. 57/58/ pp. 223-231.

Witkowski et al., "Conversion of a B-Ketoacyl Synthase to a Malonyl Decarboxylase by Replacement of the Active-Site Cysteine with Glutamine," Biochemistry, 1999, vol. 38, 11643-11650.

(56) References Cited

OTHER PUBLICATIONS

Kisselev, "Polypeptide Release Factors in Prokaryotes and Eukaryotes: Same Function, Different Structure," Structure, vol. 10, Jan. 2002, pp. 8-9.
Whisstock et al., "Predication of protein function from protein sequence and structure," Q. Rev. Biophysics, 2003, vol. 36, pp. 307-340.
Broun et al., "Catalytic Plasticity of Fatty Acid Modification Enzymes Underlying Chemical Diversity of Plant Lipids," Science, vol. 282, 1998, pp. 1315-1317.
Wishart et al., "A Single Mutation Converts a Novel Phosphotyrosine Binding Domain into a Dual-specificity Phosphatase," J. Biol. Chem. 1995, vol. 270(45), pp. 26782-26785.
International Search Report mailed Sep. 16, 2009 for Application No. PCT/US2009/004296, filed Jul. 24, 2009.
Written Opinion of the International Searching Authority mailed Sep. 16, 2009 for Application No. PCT/US2009/004296, filed Jul. 24, 2009.
Office Action mailed Nov. 14, 2012 in China Patent Application No. 200980138072.X, filed Jul. 24, 2009.
Official Action mailed Jul. 10, 2012 in Mexico Patent Application No. MX/a/2011/000934, filed Jul. 24, 2009.
Official Action mailed Mar. 5, 2013 in Mexico Patent Application No. MX/a/2011/000934, filed Jul. 24, 2009.
Duarte et al., "Glyphosate (GP) Effects with Emphasis on Aquatic Organisms," Colunbia Orinoquia, ISSN: 0121-3709, pp. 70-100, 2004.
Technical Card: Glyphosate, Document filed for the Pesticide Action Network and the Alternatives Thereof, for Latin America (RAP-AL)- Communications and Administration Office, Apr. 2008.
Department of Environment, Housing and Territorial Development Ministry, Resolution (1009), published Jun. 17, 2008.
International Search Report and Written Opinion of the International Searching Authority mailed Oct. 30, 2009 for Application No. PCT/US2009/046656, filed Jun. 8, 2009.
International Search Report and Written Opinion of the International Searching Authority mailed Aug. 12, 2009 for Application No. PCT/US2009/003819, filed Jun. 25 2009.
International Search Report and Written Opinion of the International Searching Authority mailed Dec. 20, 2010 for Application No. PCT/US2010/053265, filed Oct. 19, 2010.
Extended European Search Report mailed Mar. 19, 2013 in European Patent Application 10825551.4, filed on Oct. 19, 2010.
Minoda et al., "Improvement of Culture Conditions and Evidence for Nuclear Transformation by Homologous Recombination in a Red Alga, Cyanidioschyzon merolae 10D," Plant and Cell Physiology, vol. 45, No. 6, Jun. 2004, pp. 667-671.
Hallmann et al., "Gene Replacement by Homologous Recombination in the Multicellular Green Alga, *Volvox carteri*," Proceedings of the National Academy of Sciences in the United States of America, vol. 94, No. 14, 1997, pp. 7469-7474.
Kilian et al., "High-efficiency homologous recombination in the oil-producing alga *Nannochloropsis sp.*," Proceedings of the National Academy of Sciences of the United States of America, vol. 108, No. 52, Dec. 2001, pp. 21265-21269.
Extended European Search Report mailed Oct. 19, 2011 in European Patent Application 09759628.2, filed on Jun. 8, 2009.
Hallmann, "Algal Transgenics and Biotechnology," Transgenic Plant Journal, Global Science Books Ltd., GB, vol. 1, No. 1, Jan. 2007, pp. 81-98.

International Search Report and Written Opinion of the International Searching Authority mailed Oct. 20, 2010 for Application No. PCT/US2010/001754, filed Jun. 16, 2010.
International Search Report and Written Opinion of the International Searching Authority mailed Sep. 9, 2009 for Application No. PCT/US2009/046650, filed Jun. 8, 2009.
International Search Report and Written Opinion of the International Searching Authority mailed Jun. 15, 2011 for Application No. PCT/US2010/042666, filed Jul. 20, 2010.
Pollock, "High Carbon Dioxide Requiring Mutants of *Chlamydomonas Reinhardtll*," Created Dec. 2003, [online, retrieved Oct. 14, 2010] <http://etd.Isu.edu/docs/available/etd-0828103-114026/unrestricted/Pollock_dis.pdf>.
Drocourt: GenBank Accession No: X52869.1, created Jan. 3, 1995.
Pan: GenBank Accession No: EE109892.1, created Jun. 23, 2008.
Pan: GenBank Accession No: EE109907, created Jun. 23, 2008.
Henriquez et al.: GenBank Accession No: Q07CY9, created Oct. 31, 2006.
International Search Report and Written Opinion of the International Searching Authority mailed Oct. 16, 2012 for Application No. PCT/US2012/035633, filed Apr. 27, 2012.
Yu et al., "Construction and characterization of a normalized cDNA library of *Nannochloropsis oculata* (Eustigmatophyceae)," Chinese Journal of Oceanology and Limnology, vol. 28, No. 4, pp. 802-807, 2010.
Rose A.B., "Intron-Mediated Regulation of Gene Expression," Current Topics in Microbiology and Immunology vol. 326, Jan. 1, 2008, pp. 277-290, XP009145370, ISSN: 0070-217X.
Rose A.B., "The Effect of Intron Location on Intron-Mediated Enhancement of Gene Expression in Arabidopsis," The Plant Journal, vol. 40, No. 5, Dec. 1, 2004, pp. 744-751, XP55029911, ISSN: 0960-7412, DOI:10.1111/j.1365-313X.2004.02247.
International Search Report and Written Opinion of the International Searching Authority mailed Sep. 13, 2013 in Application No. PCT/US2013/038939 filed Apr. 30, 2013.
Notice on the First Office Action mailed May 20, 2013 in Chinese Application No. 201080058106.7 filed Oct. 19, 2010.
Examination Report mailed Feb. 20, 2013 in Australian Application No. 2009274500 filed Jul. 24, 2009.
Examination Report mailed Apr. 29, 2013 in European Application No. 09759628.2 filed Jun. 8, 2009.
Examination Report mailed Aug. 29, 2013 in Australian Application No. 2009255947 filed Jun. 8, 2009.
Examination Report mailed Sep. 19, 2013 in Australian Application No. 2010310765 filed Oct. 19, 2010.
Notice on the Second Office Action mailed Sep. 24, 2013 in Chinese Application No. 200980138072.X filed Jul. 24, 2009.
Zuo-Xi Ruan et al., Effects of Acute Glyphosate Exposure on the Growth and Physiology of *Nostoc Sphaeroides*, an Edible Cyanobacterium of Paddy Rice Fields, Acta Hydrobiologica Sinica, Jul. 2008 vol. 32, No. 4 pp. 462-468.
Office Action mailed Nov. 11, 2013 in Mexican Application No. MX/a/2011/000934 filed Jul. 24, 2009.
Lumbreras et al., "Efficient Foreign Gene Expression in *Chlamydomonas Reinhardtii* Mediated by an Endogenous Intron," The Plant Journal, vol. 14, No. 4 Jan. 1, 1998, pp. 441-447, XP001150496, ISN: 0960-7412, DOI: 10.1046/j.1365-313X.1998.00145.X.

\* cited by examiner

102 →  GGCGGTCTTTTGTCCTTTCCTCTATAGCCCACCCGTCTAGAGGGCACACGCGATGATCTTTATATCTCTTC
ATGTGTCTTTGTTTTAACTAGGATACTGCCGCGGTGAATGCCCATGCCGACAAGAGGCCAAACTCTATCTACA
CCCTTTTGACTTCTGTTGTGTTCGTAGTGTGCTTGCATGCCCTGAAAGTCCAGGCATCCCACTTGTGCT
CTAACCCATTCAAAACAGCAGAAGTGCTTAATTAAGATAGATTCATGATCTCCTGTCCCCTCCTTCTT
ACCTTTTCACAAACCTC

104 →  ACACAGAAGTCTCCACTCTTCGCCTCTAAAAACCTCTTTTTAAATT

106 →  ATGGTAAGTTCGTGCGCAGTGGGTTTTCGGATCTATATTGTCAAGATCCAGTTCAAGGTCAGGGATGTA
GATTAAGTACAGAAGGAGAAGCACAACTATACAACCAATCCTGTTGGCATCGCTCTGTCTATTTGTCGTGCGTGCA
CTCTATCTTACCAGAACCATACTATACAACCAATCCTGTTGGCATCGCTCTGTCTATTTGTCGTGCGTGCA
TGTGTCCATGCGTGTGGGGGCAGGGTTTTCGGGGTTGCGGTTGAAGGCACCTTATCAGAAAGATGCC
CTCAGAGATAGAGGTAGCCCCCTCCCCCGATCTTCGACCAGTCTCAGGCGAACACTTTCACCGTCG
TTCACCTCGTTACACACAAGGAGTAGACCCTCTGAAGTTCTAATTGTCATAAATGCCCCTCCCCCCTCCCTC
TTTCCCTTGATCTTCCCCTCCGAGCCAGATTATG

108 →  GCCAAGTTGACCAGTGCCGTTCCGGTCCTCACCGGCGCGCGACGTCGCCGAGCGCGGTCGAGTTCTGGACCGA
CCGGCTCGGGTTCTCCCCGGAGACTTCGTGGAAGACGACTTCGCCGGTGTGGTCCGGGACGACGTGACCCTGT
TCATCAGCGCGGTCCAGGACGCCGAGTGGTCGGAGGTCGCGGAGGTCGTGCCGGACAACACCCTGGCCTGGAC
GAGCTGTACGCCGAGCAGCCGTGGGGGCGGGAGTTCGCCCTGCGCGACCCTGCTGCACGCGCCCGGCCATGACCGA
GATCGGCGAGCAGCCGTGGGGGCGGGAGTTCGCCCTGCGCGACCCTGCCGCAACTGCGTGCACTTCGTGG
CCGAGGAGCAGGACTAA

110 →  GCTTCTGTGGAAGAGCCAGTGGTAGTAGCAGTAGCAGCCGCAGCACTCAGTGTTGGCGC
GAGAGATTGTCCATCCTTCTTAAACCTACCGGAAGAGAAATAAGGCCTTTCTCCCGTAGCGTCTCGTTT
GTTTGTGCTGATTGCTTGATATATGAGAGTGTTGAATTCCTGCATCATGTTTTCTCTGTAGTCCTTTCCTAC
CCCGTCATTCATTTTCTTCCCGTTCTTTTGTCACCCTTATTTTACATAAATTCTTTGTTTAT
AGTGAGAGGAAGGTAGAGAGAGGCATTGAGAGTGGAGCCGGGGAAAGGCTTGTGTGTCTTTGAAAGAAGAAG
AGAAACAGATCTGTTGAGCATTGAGAGTGGAGCCGGGGAAAGGCTTGTGTGTCTTTGAAAAGTTGT
TTAAATCACGAATCCGTTAGTTCTCATGTGTACCTCTTTCACTACATGTGATGAGAAAACAAAAGTGTGA
GGATTAATTGAAGAAAAAGAGAGTTCGACACGTCAAAACCGCCAAAAGACGTCACAAAGAACTTGATT
CTCTTTGCCGTGTTGATCCTGTCTTTTCCCCAGCTTGTTTCCTGCCACCCGTGGCACACGAGAGATGGACAAGA
TCAG

TRANSFORMATION OF ALGAL CELLS

CROSS-REFERENCE TO RELATED APPLICATIONS

The present application is a continuation of U.S. Non-Provisional patent application Ser. No. 12/480,611 filed on Jun. 8, 2009, titled "Transformation of Algal Cells," as issued on Feb. 21, 2012 as U.S. Pat. No. 8,119,859, which claims the benefit and priority of U.S. Provisional Patent Application Ser. No. 61/059,672 filed on Jun. 6, 2008, titled "VCP-Based Vector for *Nannochloropsis* Transformation," all of which are hereby incorporated by reference.

The present application is related to U.S. Non-Provisional patent application Ser. No. 12/480,635 filed on Jun. 8, 2009, titled "VCP-Based Vectors for Algal Cell Transformation," as issued on Nov. 27, 2012 as U.S. Pat. No. 8,318,482, which is hereby incorporated by reference.

REFERENCE TO SEQUENCE LISTINGS

The present application is filed with sequence listing(s) attached hereto and incorporated herein by reference.

BACKGROUND OF THE INVENTION

1. Field of the Invention

This invention relates to molecular biology, and more specifically to the transformation of algal cells.

2. Description of Related Art

Transformed algae cells may be useful in aquaculture production. The transformation of small algal cells with strong cell walls, however, is difficult to achieve. Accordingly, there is a need for improved methods of algal cell transformation.

SUMMARY OF INVENTION

Exemplary methods include a method for transforming an algal cell by preparing a transformation construct, preparing a particle for bombarding the algal cell, adhering the transformation construct to the particle, bombarding the algal cell with the particle, and growing the algal cell into a colony. The transformation construct is replicated within a nuclear genome of the algal cell and the growing of the algal cell is in a nutrient medium.

Another exemplary method may include a method for genetically modifying an algal cell, by adding nucleic acid to the algal cell while the algal cell is suspended in a solution of low conductivity, introducing the nucleic acid into the algal cell by application of an electrical pulse resulting in a transformed algal cell, and selecting a colony that includes the transformed algal cell.

BRIEF DESCRIPTION OF THE DRAWINGS

FIG. 1 shows a sequence of an exemplary transformation construct.

DETAILED DESCRIPTION OF THE INVENTION

Provided herein are exemplary methods for transforming algal cells. Transformed algae cells may be useful in aquaculture production. The transformation of small algal cells with strong cell walls, however, is difficult to achieve. Various exemplary embodiments of the present invention are useful in the efficient transformation of *Nannochloropsis*, a microalga of about 3-5 micrometers in size.

Typically, gold particles having a size of about 0.6 micrometers are used in biolistic transformation of algae smaller than about 5 micrometers. A transformation vector or transformation construct is precipitated onto the gold particles, and the gold particles carrying the transformation construct are propelled through the cell walls of the algae. The transformation efficiency of *Nannochloropsis* with this method is very low.

According to the various exemplary methods provided herein, aggregates of gold particles are broken into smaller fragments to increase transformation efficiency. Using a 1510 Branson Bath Sonicator, 0.6 micrometer gold particles are sonicated for one hour just prior to precipitating a transformation construct onto the gold particles. Using the sonicated gold particles or beads, fourteen micrograms of transformation construct may produce approximately twenty zeocine resistant transformants. Thus, this exemplary embodiment provides about a twenty-fold increase in transformation efficiency over currently available methods.

An alternative exemplary embodiment uses an improved electroporation method to transform algal cells. In electroporation, algal cells are subjected to an electric current that opens transient pores in the membranes of the algal cells. A transformation vector may pass through an open pore, eventually leading to the successful transformation of the algal cell. Using a Biorad Genpulser I electroporator set to the exponential protocol, the following electroporation conditions were used: 2200V, 500Ω shunt resistor, 50 µF capacity, 2 mm gap cuvette. When $10^9$ cells have been used in iso-osmotic non electrolyte buffer (resistance higher than 1100Ω) in a volume of 100 microliters, typical time constants τ of 20-24 ms have been reported by the device. This approach produced hundreds of zeocine resistant transformants per microgram of transformation construct used.

FIG. 1 shows the sequence of an exemplary transformation construct. The exemplary transformation construct 100 includes a promoter sequence 102, DNA encoding a transcribed but untranslated 5' region ("UTR") 104, an intron 106, a ble gene 108 and DNA encoding a 3' UTR 110. The transformation construct may comprise any number of promoters, genes, and/or other nucleic acid polymers (naturally occurring or synthetic) and/or their analogs, or other compounds that do not interfere with the ability of the transformation construct to enter the algal cell or the algal genome, or to function. In some embodiments, additional nucleotides may appear in the transformation construct to facilitate or direct the insertion of the construct (or any part thereof) into a desired location in the genome.

The various exemplary methods described herein may be employed using the exemplary transformation vectors or transformation constructs PL90, H8 and B9 as described in U.S. Non-Provisional patent application Ser. No. 12/480,635 filed on Jun. 8, 2009, titled "VCP-Based Vectors for Algal Cell Transformation," which is hereby incorporated by reference. The difference between the three exemplary vector constructs is the type of selection marker gene (SG) used: the sh ble gene (PL90), the hygromycin B phosphotransferase gene (H8), or the blasticidin S deaminase (B9) gene.

Figure 2:
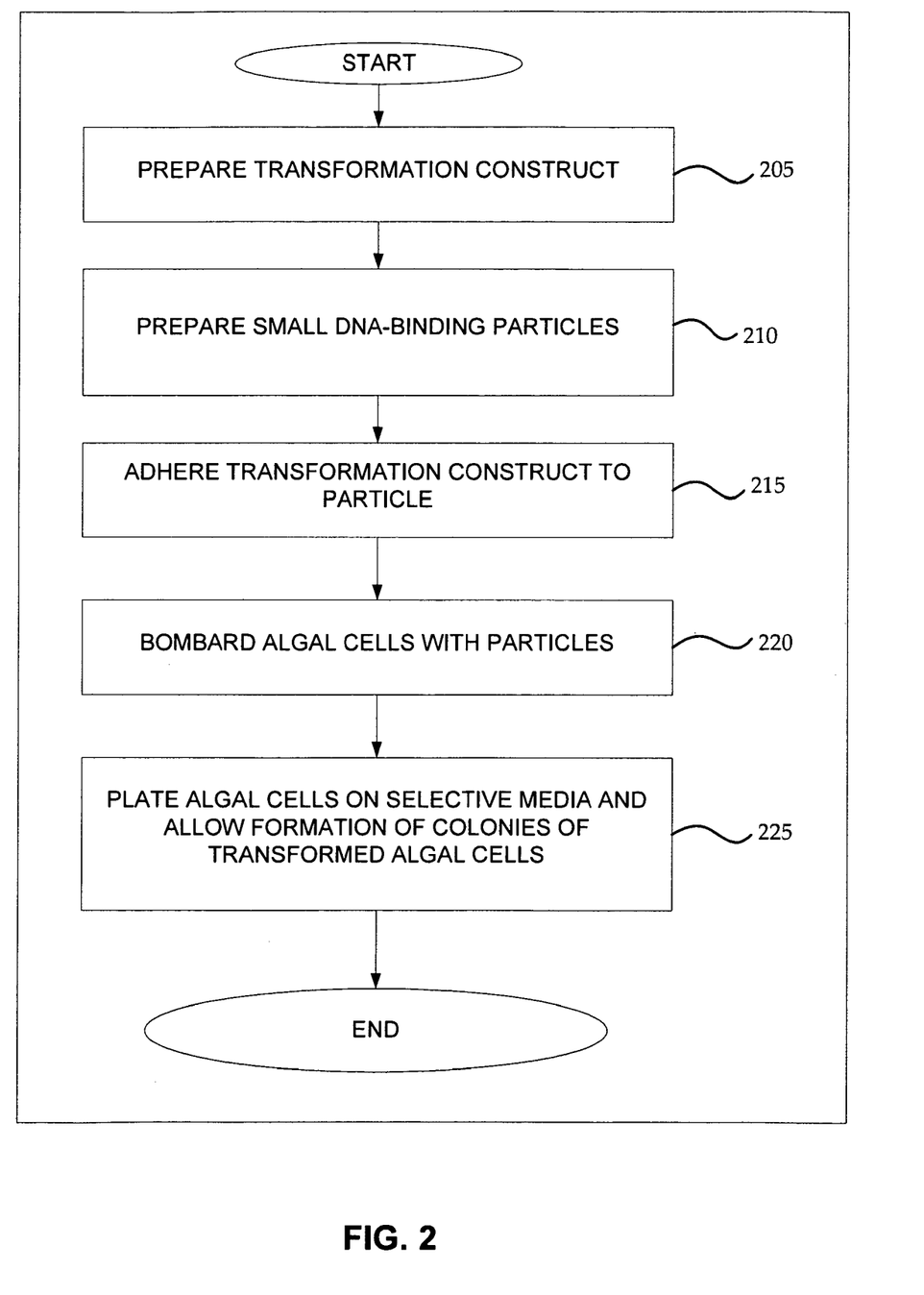
FIG. 2 illustrates an exemplary method for transforming an algal cell with a particle gun.

FIG. 2 illustrates an exemplary method for transforming an algal cell with a particle gun.

At step 205, a desired transformation construct is prepared. According to one exemplary embodiment, the transformation construct may be either the PL90 transformation vector, the H8 transformation vector, or the B9 transformation vector.

At step 210, small DNA-binding particles are prepared. According to one exemplary embodiment, 0.6 μm gold particles are sonicated in buffer for one hour.

At step 215, the transformation construct is adhered to the small DNA-binding particles. In one exemplary method, transformation constructs are precipitated onto the gold particles.

At step 220, algal cells are bombarded with the gold particles having the transformation constructs precipitated onto them. *Nannochloropsis* cells, according to one exemplary method, are bombarded with fourteen micrograms of transformation construct DNA that has been precipitated onto 0.42 mg of the 0.6 μm gold particles.

At step 225, the algal cells are grown into colonies on selective medium. According to one exemplary embodiment, if the transformed cells produce a large quantity of a desired gene product, the cells may be further processed to collect the desired product. One having ordinary skill in the art will recognize that many appropriate buffers, media, and/or methods of product collection may be used.

EXAMPLE ONE

*Nannochloropsis oceanica* cells were grown in low light (85 μE/(m2*s)) to mid log phase in F2 media, 50% seawater (See e.g., Guillard, R. R. L. and Ryther, J. H. 1962. Studies of marine planktonic diatoms. I. Cyclotella nana Hustedt and Detonula confervacea Cleve. Can. J. Microbiol. 8: 229-239). *Nannochloropsis* cells were then pelleted at 2500 g for 15 minutes. The pellet was then resuspended in fresh media. $5*10^9$ resuspended cells were spread on petri dishes (F2 media, 50% seawater, 1% Bactoagar™ from DIFCO) and allowed to dry. 0.6 μm gold particles (Biorad) were coated essentially as recommended by Biorad with transformation vector PL90. The plated cells were then bombarded with microparticles (coated with transformation construct DNA as recommended by Biorad) by a particle gun (Biolistic PDS-1000/He particle gun Bio-Rad) at vacuum pressure of 29 mm Hg utilizing the heptameric adapter from Biorad. All different stages were used in combination with 3 different rupture discs (1100 PSI, 1350 PSI, 1550 PSI) provided by Biorad. Cells were subsequently resuspended in 10 ml fresh F2 Medium (half salinity) and allowed to recover overnight under low light (~10-25 μE/(m2*s)). $0.5*10^7$ cells were then plated on agar plates (0.8% Bactoagar™ from DIFCO) containing the selection agent (2 μg/ml zeocine, 300 μg/ml hygromycin or 50 μg/ml blasticidin, depending on the transformation construct used) and incubated at 25° C. at −50 μE/(m2*sec). Negative control DNA was linearized pJet1 vector DNA (Fermentas). Growth of colonies could be observed after ~2-3 weeks. Colonies were then analyzed for the presence of the selection marker gene. Colonies on selective media were never obtained in experiments utilizing the control DNA. Only utilization of 1350 PSI rupture disc, stage 1 (uppermost stage, just underneath heptameric adapter) and 1550 PSI rupture disc stage 2 yielded a few transformants under these conditions.

To proof for the presence of transformation construct within the cells (and thus that the transformation experiment was a success), a single colony was picked and restreaked on unselective medium and allowed to grow for approximately one week. Cells were then scraped (~10 μg cells), washed 3 times in F2-50% seawater, incubated with 30 units DNAse I in DNAse I buffer (Fementas) 1 hour at 37° C. Cells were then washed once in F2-50% seawater and resuspended in 50 μl F2-50% seawater. Cells were pelleted and the supernatant collected; cells were resuspended in 50 μl ddH20. Cell and supernatant fractions were incubated 7 minutes at 95° C.; 5 μl each fraction were subjected to PCR (50 μl reaction volume) with specific primers against the ble gene (rev: 5'TTA GTC CTG CTC CTC GGC CAC GAA3', for: 5'ATG GCC AAG TTG ACC AGT GCC GT3').

The PCR program was:
1. 94° C., 3 min, 1 cycle;
2. 94° C., 15 sec;
3. 58° C., 30 sec;
4. 72° C., 30 sec (steps 2-4 are amplification stage, 38 cycles);
5. 72° C., 5 min; and
6. 4° C., cool down and keep temperature.

Figure 3:
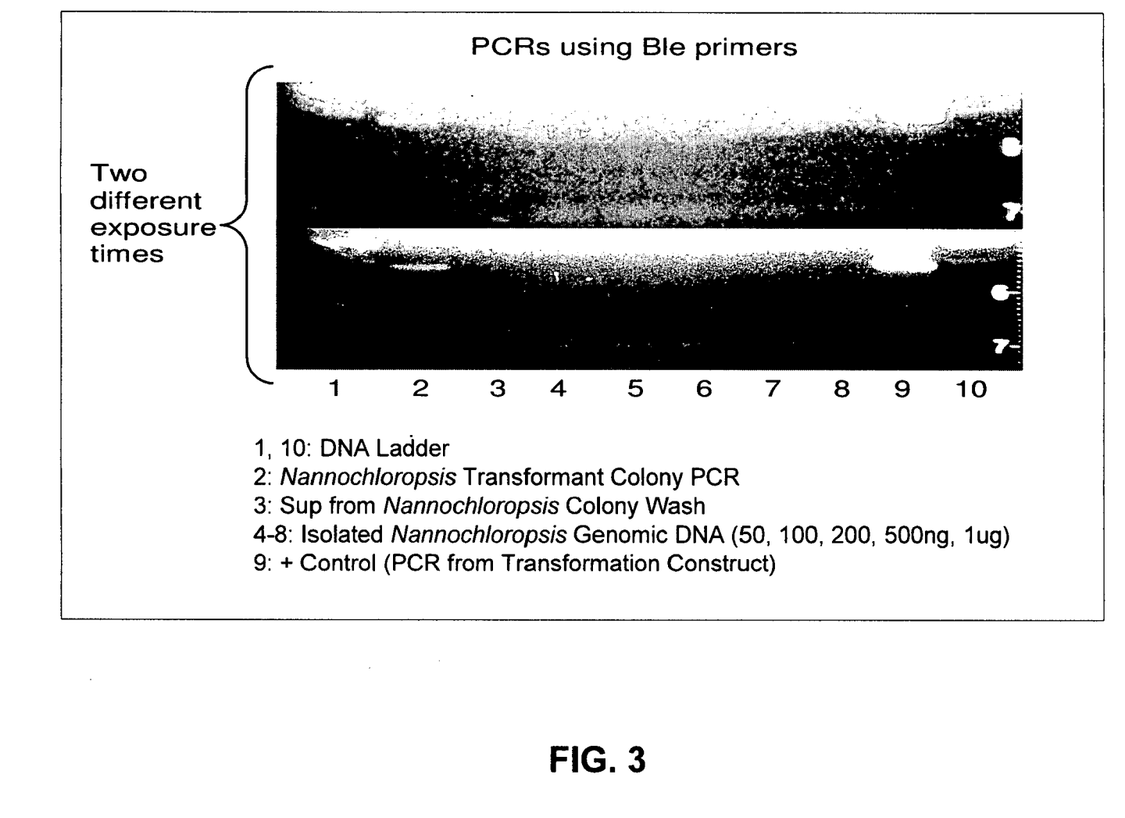
FIG. 3 shows an exemplary polymerase chain reaction result obtained using ble primers as described in connection with Example One.

FIG. 3 shows the exemplary polymerase chain reaction result obtained using ble primers as described in connection with Example One.

EXAMPLE TWO

We followed the procedures of Example One, except this time utilizing a 1510 Branson Bath Sonicator, 0.6 μm gold particles were sonicated for 1-hour just prior to DNA precipitation onto beads. Using the sonicated beads, 14 μg DNA produced approximately 20 zeocine-resistant transformants.

Detailed Procedure.

Growth and preparation of cells: the cells were grown in 2 L flasks in F2 medium (containing seawater of half salinity) to early log phase. The cells were then harvested by centrifugation for 10 min. at 2500 and gently resuspended in fresh F2 medium. $5*10^9$ cells (in ~400 μl) were then plated on an agar plate (containing 1% Bactoagar™ from DIFCO) and allowed to dry for ~20 minutes in a sterile hood.

Preparation of Particles.

Different sizes and materials of particles were used (all obtained from Biorad), i.e. Tungsten particles 0.7 and 1 μm average diameter and gold particles 1 μm or 0.6 μm average diameter. Prior to the precipitation of the DNA onto the particles (the micro carrier), the particles were resuspended in ddH2O and sonicated for 1 hour in a 1510 Branson Bath Sonicator. 3 mg particles were coated with 100 μg linearized transformation construct DNA as described elsewhere (see user manual Biolistic PDS-1000/He particle gun from Bio-Rad) and resuspended in 500 μl Ethanol after 2 washing steps in the same volume ethanol. 10 μl of this DNA coated particle solution ('the microcarrier') was pipetted onto each macrocarrier which was fitted subsequently into the Hepta Adapter (optional component of the Biolistic® PDS-1000/He Particle Delivery system). Thus, each shot with the particle gun provided 7×2 μg=14 μg DNA precipitated on micro carrier. Coated particles were used for biolistic transformation within an hour.

Delivery of Particles to Cells.

The petri dish containing the cells was placed on the corresponding stage within the particle delivery system (stage 1 being the nearest to the heptamer adapter, stage 3 being the one most far away). One of three different rupture discs (Biorad) was used: 1100 psi, 1350 psi, 1550 psi. Vacuum was generally applied to 29 mm Hg (obtained within ~20 sec.) and the He pressure was increased at max speed in order to provide the He shock wave after rupture of the rupture disc. The pressure in the delivery chamber was instantly increased at maximal rate (less than 10 sec until atmospheric pressure was reached) and the petri dish with the bombarded cells was recovered.

Post Delivery Treatment of Cells.

The cells were gently scraped off the plate resuspended in 10 ml of F2 medium (half salinity compared to seawater) and allowed to recover in low light (~10 μE/(m2*s)) over night. The next day, 0.5*10^7 cells were plated on F2 agar plates (petri dish, F2 medium with half salinity compared to seawater and 0.8% Bactoagar™ from DIFCO) and the respective selection agent. Plates were incubated at 25° C. at 50 μE/(m2*sec). Colonies were visible after ~2-3 weeks.

Results.

1. From all the particles tested, only the 0.6 μm gold particles produced transformants.
2. We tested all different combinations of stage position (within the particle delivery system) and rupture disc.
3. A major difference was observed when we pretreated the gold particles with ultrasound.

The following table reflects the quantity of transformants observed when using different experimental parameters. The vector used in these experiments was PL90 conferring resistance against the drug zeocine.

| | Gold particles pretreatment[1] | | | | | |
|---|---|---|---|---|---|---|
| | no | no | no | yes | yes | yes |
| | Rupture disc | | | | | |
| | 1100 psi | 1350 psi | 1550 psi | 1100 psi | 1350 psi | 1550 psi |
| Stage 1 | 0 | 1 | 0 | 11 | 4 | 17 |
| 2 | 0 | 0 | 2 | 25 | 4 | 22 |
| 3 | 0 | 0 | 0 | 8 | 4 | 5 |

[1]gold particles were washed and then disrupted by 1 hour ultrasound treatment.

These results indicate that:

1. Pretreatment of the 0.6 μm gold particles by ultrasound dramatically increases the transformation efficiency.
2. The transformation efficiency is highest at 1100 Psi pressure (rupture disc) and if the petri dish containing the cells is localized on stage 2.
3. The vector PL90 may be used for the nuclear transformation of *Nannochloropsis* by conferring resistance against the drug zeocine.

Figure 4:
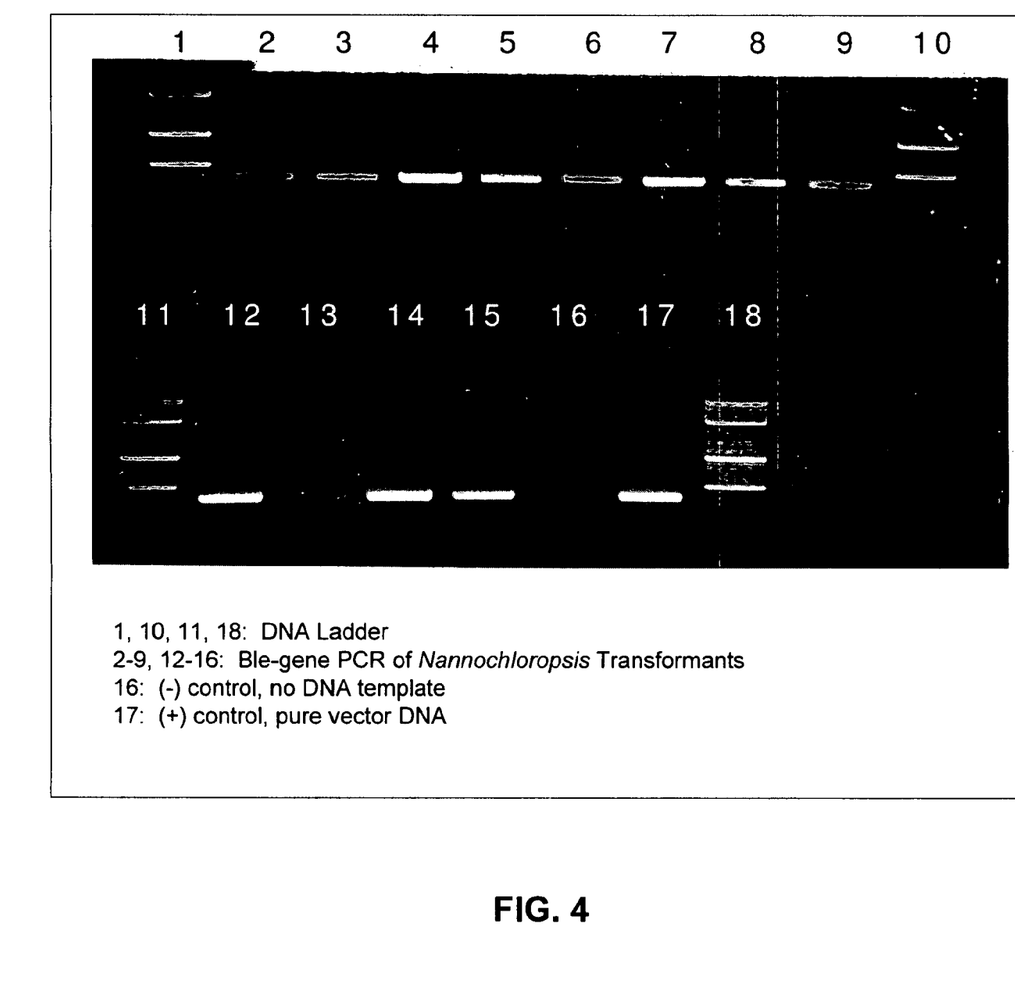
FIG. 4 shows the exemplary polymerase chain reaction result obtained as described in connection with Example Two.

FIG. 4 shows the exemplary polymerase chain reaction result obtained as described in connection with Example Two.

EXAMPLE THREE

Transformation via electroporation.
Detailed procedure.
Growth and preparation of cells.

*Nannochloropsis oceanica* was grown in 2 L flasks in F2 medium (containing seawater of half salinity) to mid log phase. The cells were then harvested by centrifugation for 10 min. at 2500 and gently resuspended in 375 mM sorbitol. The cells were washed several times in 375 mM sorbitol solution in order to minimize conductivity of remaining medium. The cells were finally resuspended to a final concentration of 10^10 cells/ml and used for transformation within an hour.

Electroporation.

Electroporation was performed in a Biorad GenPulser I Electroporator utilizing 2 mm cuvettes. 100 μl cells at 10^10 cells/ml were pipetted into a 2 mm cuvette and varying amounts of transformation construct in <5 μl volume ddH2O were added. The cuvette containing the DNA-cell mixture was gently snipped for mixing and then placed into the electroporation chamber.

Device settings were exponential decay protocol with 500 Ohm Shunt resistance and 50 μF capacity, 2 mm Gap.

Post Delivery Treatment of Cells.

After electroporation the cells were allowed to stay in the cuvette for 3 minutes before they were recovered and resuspended in 10 ml F2 medium (half salinity). After an overnight incubation in low light (~10 μE/(m2*s), 0.5*10^7 cells were plated on F2 agar plates and the respective selection agent. Plates were incubated at 25° C. at 50 μE/(m2*sec). Colonies were visible after ~2-3 weeks.

Results.

In initial experiments, we used 0.5 μg DNA/100 μl cell suspension and varied the voltage. We routinely measured electrical resistance of the cell-DNA mixture with the respective option in the Biorad GenPulser I Electroporator to ensure that resistance was >1100 Ohm. The actual electroporation usually returned exponential decay times τ of 20-24 ms. Initially, when performing these experiments with varying field strengths we got a single transformant (again we used the PL90 vector linearized and performed selection on agar plates containing zeocine) at the highest field strength initially tried (which was 1000V, =5 kV/cm). 5 kV/cm is a very high field strength and we did not expect that we might obtain transformants at all at such a high field strength. Since we obtained a single transformant at this high voltage we performed electroporations in additional experiments at very high voltages.

Figure 5:
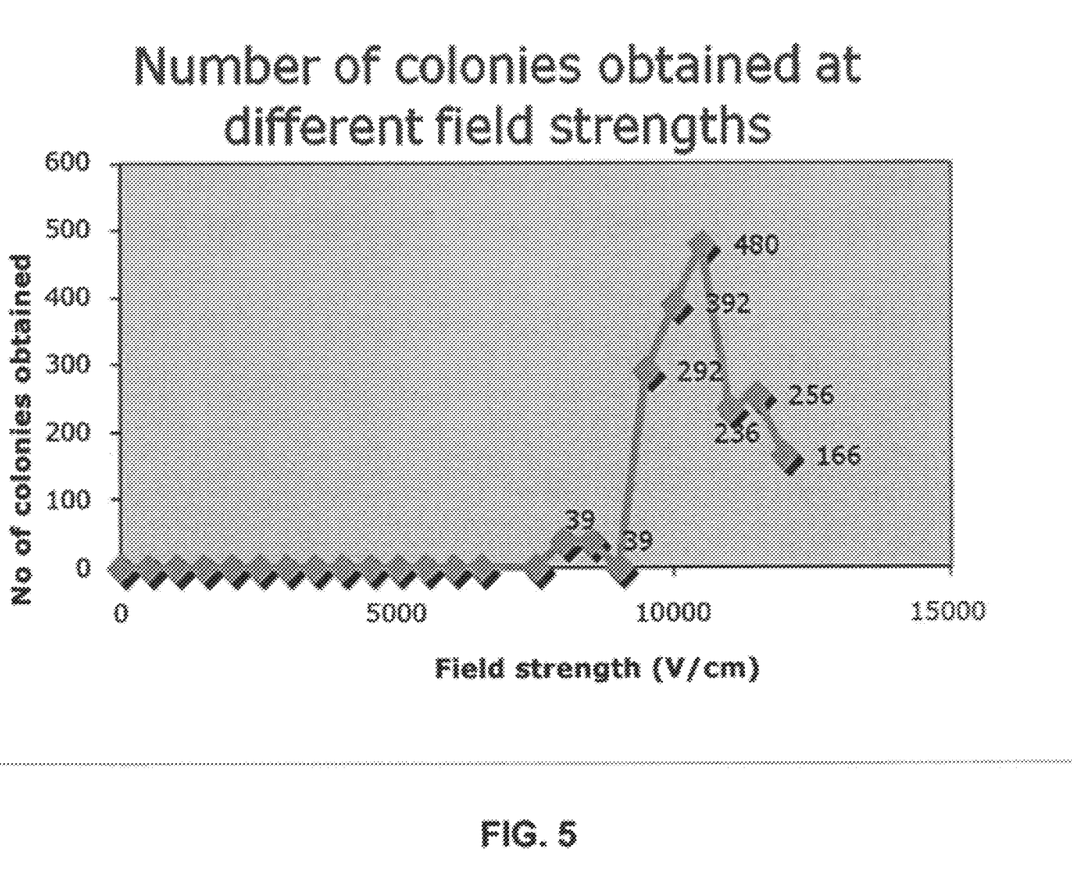
FIG. 5 shows the number of algal cell transformants obtained based on the field strength of electroporation applied to perform the transformation as described in connection with Example Three.

FIG. 5 shows the number of algal cell transformants obtained based on the field strength of electroporation applied to perform the transformation as described in connection with Example Three. The result of this experiment as shown in FIG. 5 was very surprising: transformation was successful at field strengths equal or higher than 8 kV/cm and efficiency peaked at 10.5 kV/cm. Note that applied field strengths for the electroporation of algae are typically a factor of 10 lower. Higher field strengths than 12000V/cm were not possible to apply (cuvettes arced).

We conclude that we can transform *Nannochloropsis* with the vector PL90 if we treat the cells as indicated above.

EXAMPLE FOUR

Ideal Electroporation.

Parameters are (within Biorad GenPulser I Electroporator): 10^9 cells in 100 μl 375 mM sorbitol (washed several times), 500 Ohm shunt resistor, 2 mm gap cuvette, 10500 volt/cm (=2100V/2 mm), exponential decay program.

We then tested the efficiency of transformation by adding varying amounts of DNA to the electroporation cuvette (again containing 10^9 cells in 100 μl).

Figure 6:
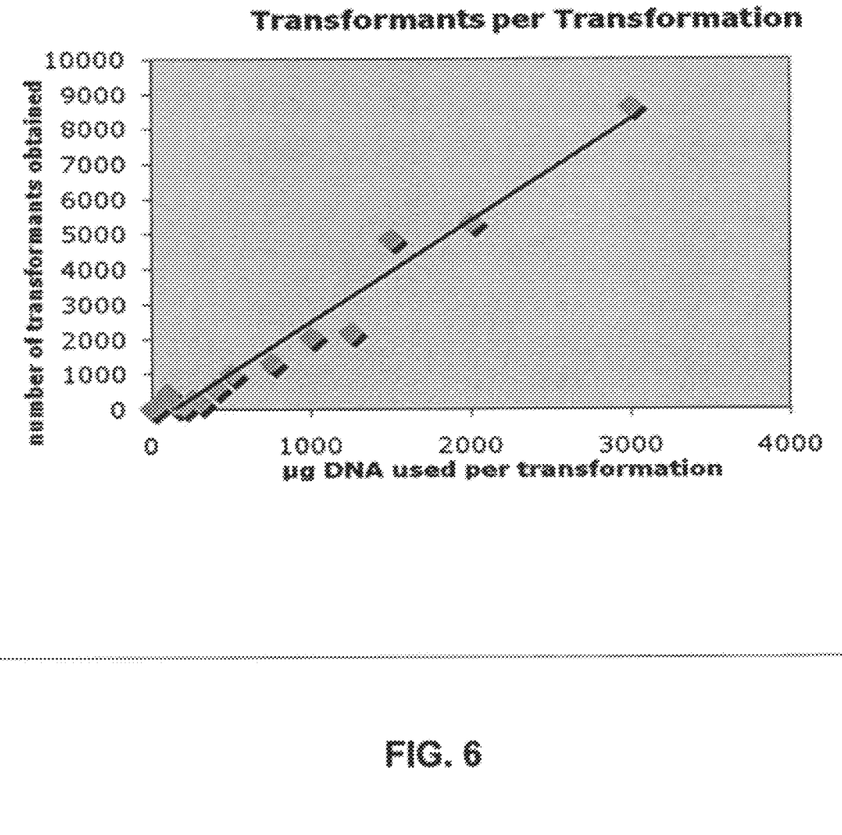
FIG. 6 shows the number of transformants obtained under exemplary optimal electroporation conditions, while varying the amount of transformation construct DNA used as described in connection with Example Four.

FIG. 6 shows the number of transformants obtained under exemplary optimal electroporation conditions, while varying the amount of transformation construct DNA used as described in connection with Example Four. We observed a linear increase in the number of transformants obtained based on increasing the amount of transformation construct DNA used. For example, 3 μg of transformation construct DNA added during a single electroporation experiment yielded approximately 9000 transformants, 1.5 µg of transformation construct DNA yielded approximately 4500 transformants. This result indicates that no saturation with DNA occurred and that the transformation method via electroporation which we established is extremely efficient.

Figure 7:
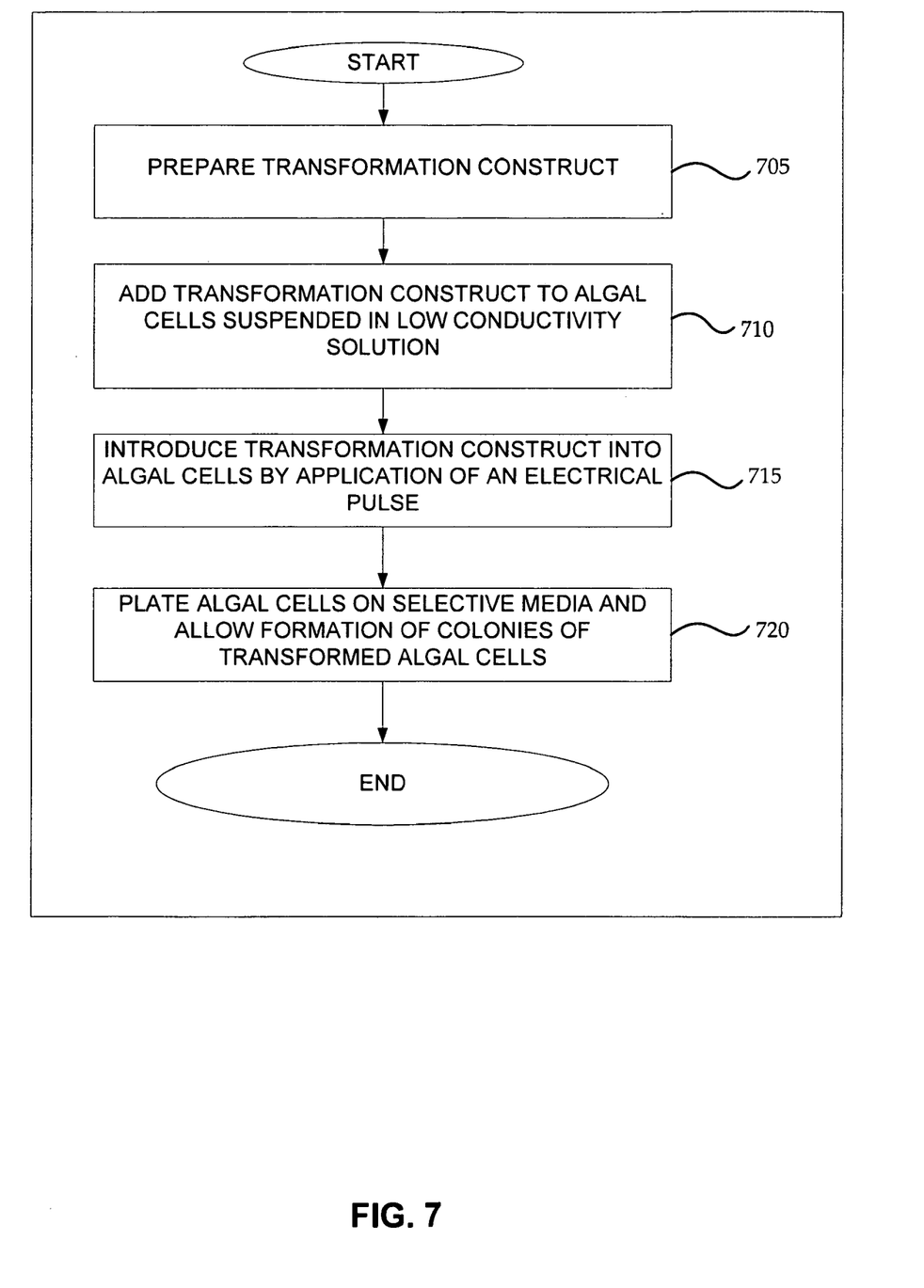
FIG. 7 illustrates an exemplary method for transforming an algal cell with electroporation.

FIG. 7 illustrates an exemplary method for transforming an algal cell with electroporation.

At step 705, a desired transformation construct is prepared. According to one exemplary embodiment, the transformation construct may be either the PL90 transformation vector, the H8 transformation vector, or the B9 transformation vector.

At step 710, the transformation construct is added to algal cells, while the algal cells are suspended in a solution of low conductivity. In various exemplary embodiments, the solution is a sorbitol solution.

At step 715, the transformation construct is introduced into the algal cells by application of an electrical pulse, resulting in transformation of the algal cells. According to some exemplary embodiments, the electrical pulse is applied with a field strength of higher than approximately 10,000 V/cm, and with a shunt resistor of greater than approximately 100 OHM.

At step 720, the algal cells are grown into colonies on selective medium. According to one exemplary embodiment, if the transformed cells produce a large quantity of a desired gene product, the cells may be further processed to collect the desired product. One having ordinary skill in the art will recognize that many appropriate buffers, media, and/or methods of product collection may be used.

While various embodiments have been described above, it should be understood that they have been presented by way of example only, and not limitation. Thus, the breadth and scope of a preferred embodiment should not be limited by any of the above-described exemplary embodiments.

What is claimed is:

1. A method for genetically modifying an algal cell, the method comprising:
    adding nucleic acid to the algal cell while the algal cell is suspended in a solution of low conductivity, the nucleic acid including a gene involved in lipid biosynthesis;
    introducing the nucleic acid into the algal cell by application of an electrical pulse resulting in a transformed algal cell; and
    selecting a colony that includes the transformed algal cell;
    wherein the electrical pulse is applied with a field strength of higher than approximately 7500 V/cm; and
    wherein the algal cell is of genus *Nannochloropsis*.

2. The method of claim 1, wherein the nucleic acid includes a transformation construct.

3. The method of claim 1, wherein the electrical pulse is applied with a field strength of higher than approximately 9000 V/cm.

4. The method of claim 1, wherein the electrical pulse is applied with a field strength of higher than approximately 10,000 V/cm.

5. The method of claim 1, wherein the electrical pulse is applied with a shunt resistor of greater than approximately 100 OHM.

* * * * *

SEQUENCE LISTING

<160> NUMBER OF SEQ ID NOS: 1

<210> SEQ ID NO 1
<211> LENGTH: 1820
<212> TYPE: DNA
<213> ORGANISM: Nannochloropsis

<400> SEQUENCE: 1

```
ggcggtcttt tgtcctttcc tctatagccc acccgtctag agggcacacg cgatgatctt      60
tatatctctt catgtgtctt tgttttaact aggatactgc cgggtgaatg cccatcggac     120
aagaggccaa actctatcta cacccttttg acttctgttg tggtcgtagt gtgtgcttgc     180
atgccctgaa agtccaggca tcccacttgt gctctaaccc cattcaaaac agcagaagtg     240
cttaattaag atatagattc atgatctcct gtcccctcct tcttacctt tcacaaacct     300 cacacagaag tctccactct tcgcctctaa aacctctttt taaattatgg taagttcgtg     360
cggcagtggg ttttcggatc tatatttgtc aagatccagt tcaaggtcag ggatgtagat     420
taagtacaga aggagaagca caagcgcgcc agttcgcccc tcacggcctg gagcagggca     480
tttaatccct ctatcttacc agaaccatac tatacaacca atcctgttgg catcgctctg     540
tctatttgtc gtgcgtgcat gtgtccatgg tgtggtgggg ggcaggggtt ttcggggttg     600
cggttgaagg caccttatca gaaagatgcc ctcagagata gaggtagccc cctcccccg      660 atcttcgacc agtcctgtca ggcgaacact ttcacccgtc gttcacctcg ttacacacaa     720
ggagtagacc tctgaagttc taattgtcat aaatgcccct cccccctccc tctttccctt     780
gatcttcccc tccgagcaga ttatggccaa gttgaccagt gccgttccgg tgctcaccgc     840
gcgcgacgtc gccggagcgg tcgagttctg gaccgaccgg ctcgggttct cccgggactt     900
cgtggaggac gacttcgccg gtgtggtccg ggacgacgtg accctgttca tcagcgcggt     960
ccaggaccag gtggtgccgg acaacaccct ggcctgggtg tgggtgcgcg gcctggacga    1020
gctgtacgcc gagtggtcgg aggtcgtgtc cacgaacttc cgggacgcct ccgggccggc    1080
catgaccgag atcggcgagc agccgtgggg gcgggagttc gccctgcgcg acccggccgg    1140
caactgcgtg cacttcgtgg ccgaggagca ggactaagct tctgtggaag agccagtggt    1200
agtagcagta gcagcagcag tagcagccgc agcactcagt gttggcgcga gagattgtcc    1260
atcccttctt aacctaccgg aagagaaata aggcctttct cccgtagctg tcttcgtttg    1320
tttgtgctga ttgcttgata tgagagtgtt gaattcctgc atcatgtttt tctctgtagt    1380
```

-continued

| | | | | | |
|---|---|---|---|---|---|
| cctttcctac | ccccgtcatt | ttctttctc | cctggttctt | cttttgtcac | ccttatttta | 1440
| cataaaattt | tctttgttta | tagtgagagg | aaggtagaga | ggggaaaaca | agaacaacga | 1500
| acgcaagcgt | gtgaaaggag | ggcgagtaga | agagaaacag | atctgttgag | cattgagagt | 1560
| ggagccgggg | gaaaggcttg | tgtgttgtct | ttgaaaaagt | tgtttaaatc | acgaatccgt | 1620
| tagttctcat | gtgtacctct | ttcactacat | gtgatggaga | aaacaaaagt | gtgaggatta | 1680
| attgaagaaa | aagaagagtt | cgacacgtca | aaccgcccaa | aagacgtcac | aaagagaact | 1740
| tgattctctt | tgccgtgttg | atcctgtctt | ttcccccagc | ttttcttgcc | acccgtggca | 1800
| cacgagatgg | acaagatcag | | | | | 1820